United States Patent [19]
Lauterbach et al.

[11] Patent Number: 5,562,706
[45] Date of Patent: Oct. 8, 1996

[54] DEVICE FOR COSMETIC AND RELAXATION TREATMENT

[75] Inventors: Antonin Lauterbach, Novy Bydzov; Bohumil Myslivec, Hradec Kralove; Jiri Jerabek, Prague, all of Czech Rep.

[73] Assignee: Electro Anti Age, Inc., Québec, Canada

[21] Appl. No.: 371,373

[22] Filed: Jan. 11, 1995

[51] Int. Cl.$^6$ .................................................. A61N 2/08
[52] U.S. Cl. ............................................................ 607/3
[58] Field of Search ................................ 607/3; 600/9, 11, 600/13, 14

[56] References Cited

U.S. PATENT DOCUMENTS

| | | |
|---|---|---|
| 4,727,857 | 3/1988 | Hörl . |
| 5,085,626 | 2/1992 | Frey .......................................... 600/13 |
| 5,085,627 | 2/1992 | Fedorov et al. ............................ 600/9 |

Primary Examiner—William E. Kamm
Assistant Examiner—Scott M. Getzow
Attorney, Agent, or Firm—Robic

[57] ABSTRACT

The device is used for cosmetic and relaxation treatment involving physical factors acting synergistically, including magnetic field, electrostimulation and photostimulation. The device has a plurality of magnets mounted on a rotor, which is mounted on a shaft driven by a motor. The motor and the rotor are within a housing. The rotor and the magnets extend close to an aperture in the housing and preferably closed by a device head. In use, when the motor is off, the magnets generate a static magnetic field. When the motor is on, the magnets generate a dynamic magnetic field. Such magnetic fields have benefic relaxing effects over the body by improving microcirculation of blood vessel. The device may also comprise electrodes and light emitting diodes mounted on its head and connected to a generator of electrical impulses for electrostimulating and photostimulating the body. This device, preferably made of plastic material, is of light weight and has the advantage of being portable.

10 Claims, 6 Drawing Sheets

DEVICE FOR COSMETIC AND RELAXATION TREATMENT

FIELD OF THE INVENTION

The present invention relates to a device for cosmetic and relaxation treatment and more particularly to a device combining magnetic field treatment, electrostimulation and photostimulation.

BACKGROUND OF THE INVENTION

Over the past decades, a plurality of devices for cosmetic and relaxation treatment using a number of physical factors acting synergistically has been proposed. Some of these devices use vibrations, electrical stimulation, ozone, high voltage, either alone or in combination. Devices in this field have been proposed which are combining effect of light face massage, static magnetic field and warm air. Lasers or non-coherent light generators have also been proposed for the treatment of the so called "wine spots". In all these devices, except for the lasers, mechanical influence such as massage influence with the head of the device must be taken into account.

It is known that magnetic fields have benefic relaxing effects over the body, essentially because they improve the microcirculation in both the blood and lymphatic capillary bed, provide antioxidant activation mechanisms and have antiphlogistic effects. These effects contribute to enhance regeneration of the skin exposed. Moreover, time-varying magnetic fields have more pronounced effects compared with static ones. However, static magnetic fields are more gentle.

It is also known in the field of cosmetic and relaxation treatment that electrical stimulation, depending on the stimulus intensity, improves the circulation in muscles by causing muscle contractions followed by relaxation. Moreover, electrogymnastic improves muscle tonus. In cases of weak electrical stimulation, subcutaneous muscles are generally stimulated with all the above-mentioned consequences.

Light of suitable wavelength has also stimulating effects on metabolic processes of the exposed tissues.

Soft frequent vibrations have benefic relaxing effects by acting non-specifically and mainly on capillary bed. After a short exposure, such as a few minutes, to soft frequent vibrations, vasoconstriction can be expected on some persons, followed by vasodilatation. In most cases, direct vasodilatation can be expected.

Massage of the skin surface itself, depending on the force applied, improves mainly lymphatic drainage.

Contemporary considerations on biological response to physical factors stress out beneficial action of their combination regardless of their non-specific activity per se.

Except for the above-mentioned facts, it is necessary to consider a suitable low-frequency modulation of factors applied. In fact, low frequency modulation has effective stimulus on cellular membrane and mainly on membrane permeability changes to various ions. This effect results in the changes of metabolic activity of the exposed cells. This effect occurs not only in low frequency magnetic fields but also in cases of modulated radio and light waves.

Prior art attempts for providing cosmetic and relaxing devices involving physical factors generally relate to devices bringing into play only one factor. Additionally, these devices are not provided with means for absorbing the vibrations of the device. Therefore, strong vibrations are transferred to the hand of the user.

Examples of prior art devices are shown in U.S. Pat. Nos. 4,727,857 and 5,085,626.

There is thus a need for a device for cosmetic and relaxation treatment combining a plurality of physical factors. There is also a need for such a device which is easy to use and comfortable for the user.

SUMMARY OF THE INVENTION

An object of the present invention is to provide a device for cosmetic and relaxation treatment involving static and rotating magnetic fields, gentle vibrations with relatively high frequency and massage effect.

This device comprises a housing and a plurality of magnets mounted on a rotor which is axially mounted onto a shaft driven by a motor. The motor and the rotor are located within the housing, the motor being resiliently fastened to the housing. The housing is also provided with an aperture which is closely facing the rotor.

Preferably, the device further comprises an inner casing in which the motor is rigidly mounted, and a device head, connected to the inner casing, closing the aperture of the housing. Preferably, the housing further comprises a handle which may contain a battery, a potentiometer and switches for controlling the motor and the generator. Such handle allows easy manipulation of the device by making it portable.

In use, when the motor is off, the magnets create a static field with no vibration. When the motor is on, the magnets are rotated for creating a dynamic magnetic field with gentle vibrations transferred to the device head. Since the motor is resiliently fastened to the housing, a minimum of energy is transferred to the hands of the user holding the housing, thereby improving comfort and reducing damping.

Another object of the invention is to provide a device which further comprises electrical stimulation of the skin with electrodes mounted on the device head and connected to an electrical impulse generator. Whenever required, the generator may be switched on for stimulation of the skin.

Another object of the invention is to provide a device which additionally involves photostimulation of the skin. This device further comprises light emitting diodes (LEDs) mounted on the device head for photostimulation of the exposed area. These LEDs are connected to the same generator as the electrodes or to another one. This embodiment of the invention has the advantage of combining the effects of rotating magnetic field, electrical stimulation, gentle massage and photostimulation of the skin in a single device.

A non restrictive description of preferred embodiments of the invention will now be given with reference to the appended drawings.

DESCRIPTION OF A PREFERRED EMBODIMENT

Figure 1:
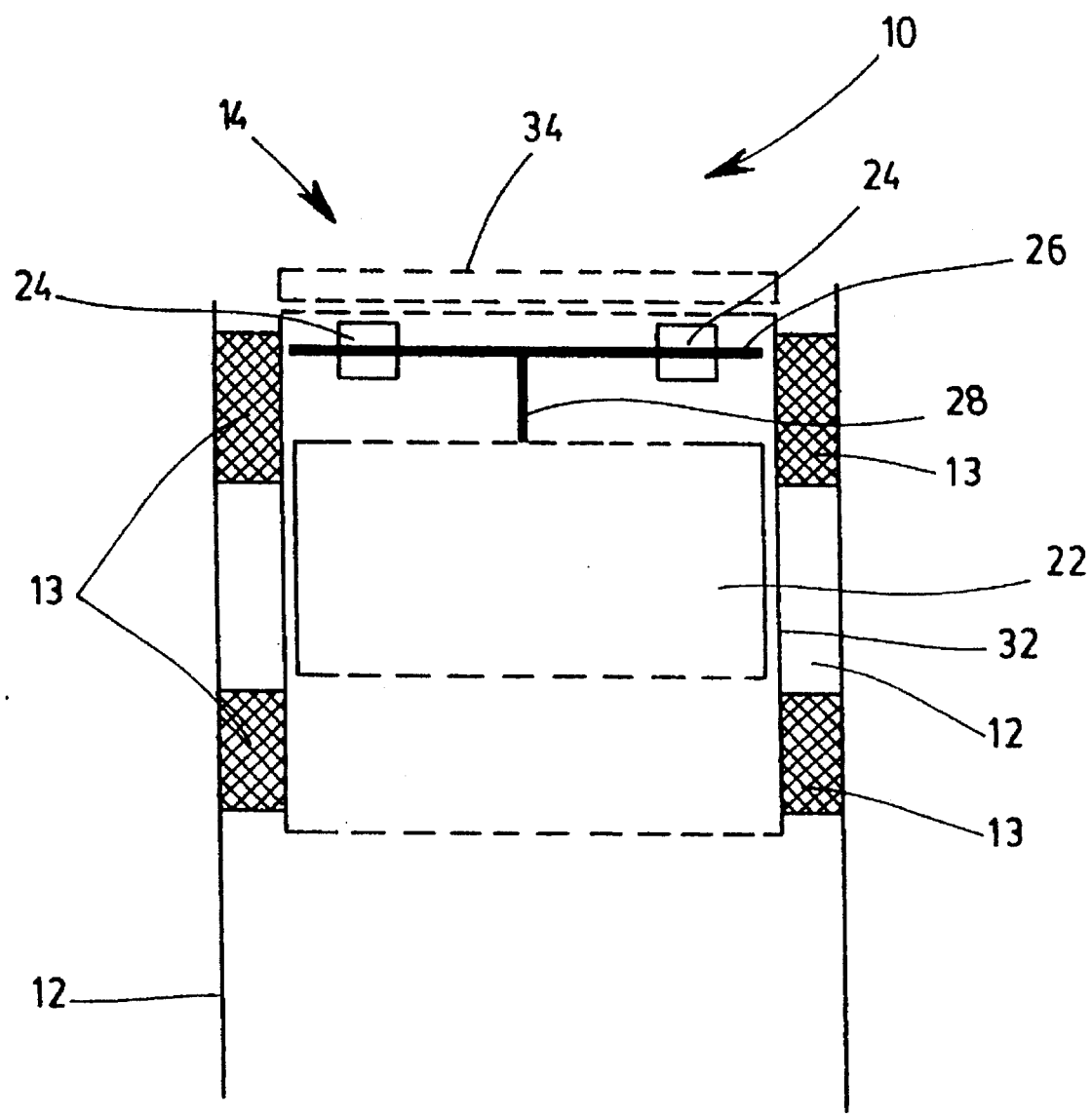
FIG. 1 is a schematic cross-sectional view of the basic components of a device for cosmetic and relaxation treatment according to the present invention.
Figure 2:
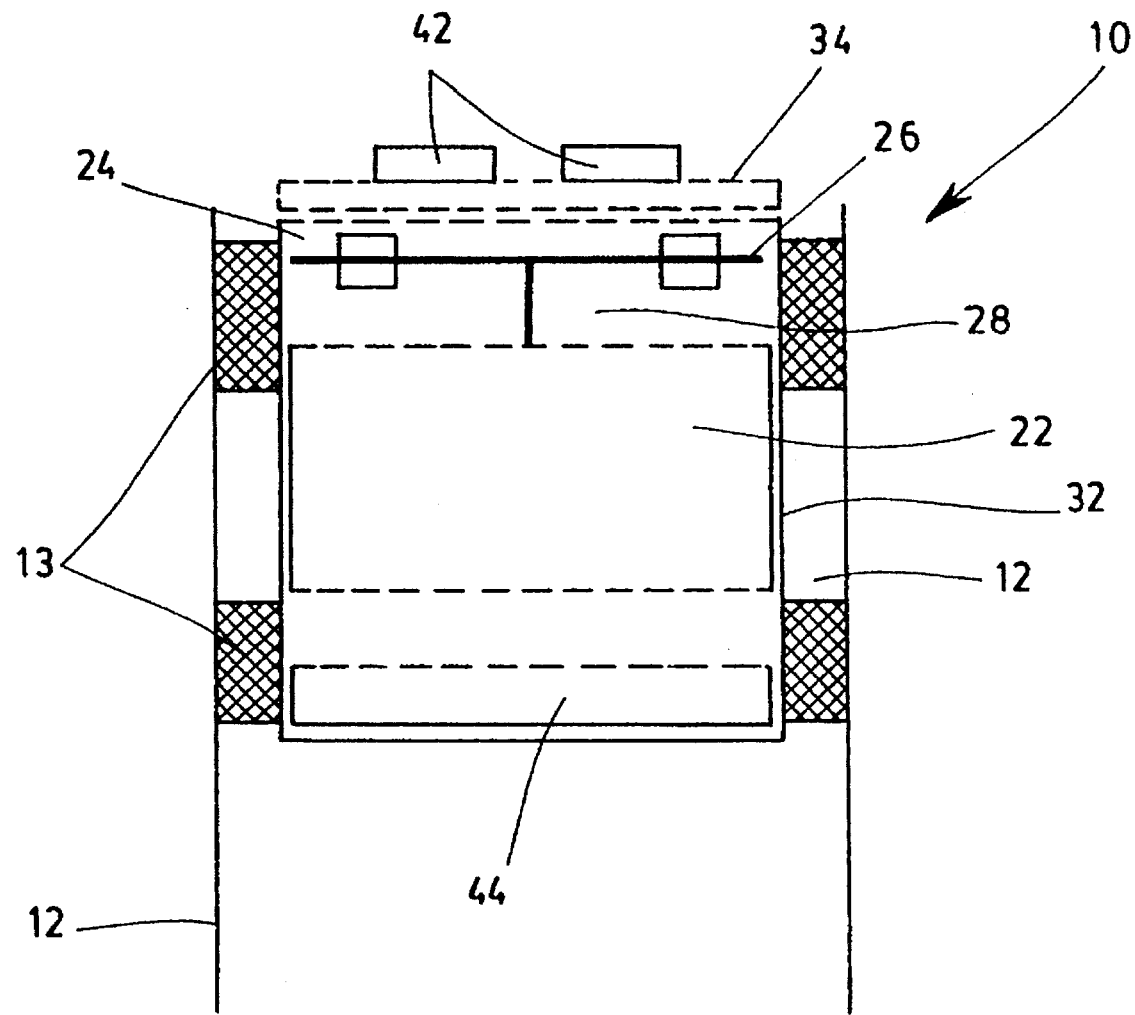
FIG. 2 is a schematic cross-sectional view, similar to FIG. 1, of another embodiment of the present invention.
Figure 3:
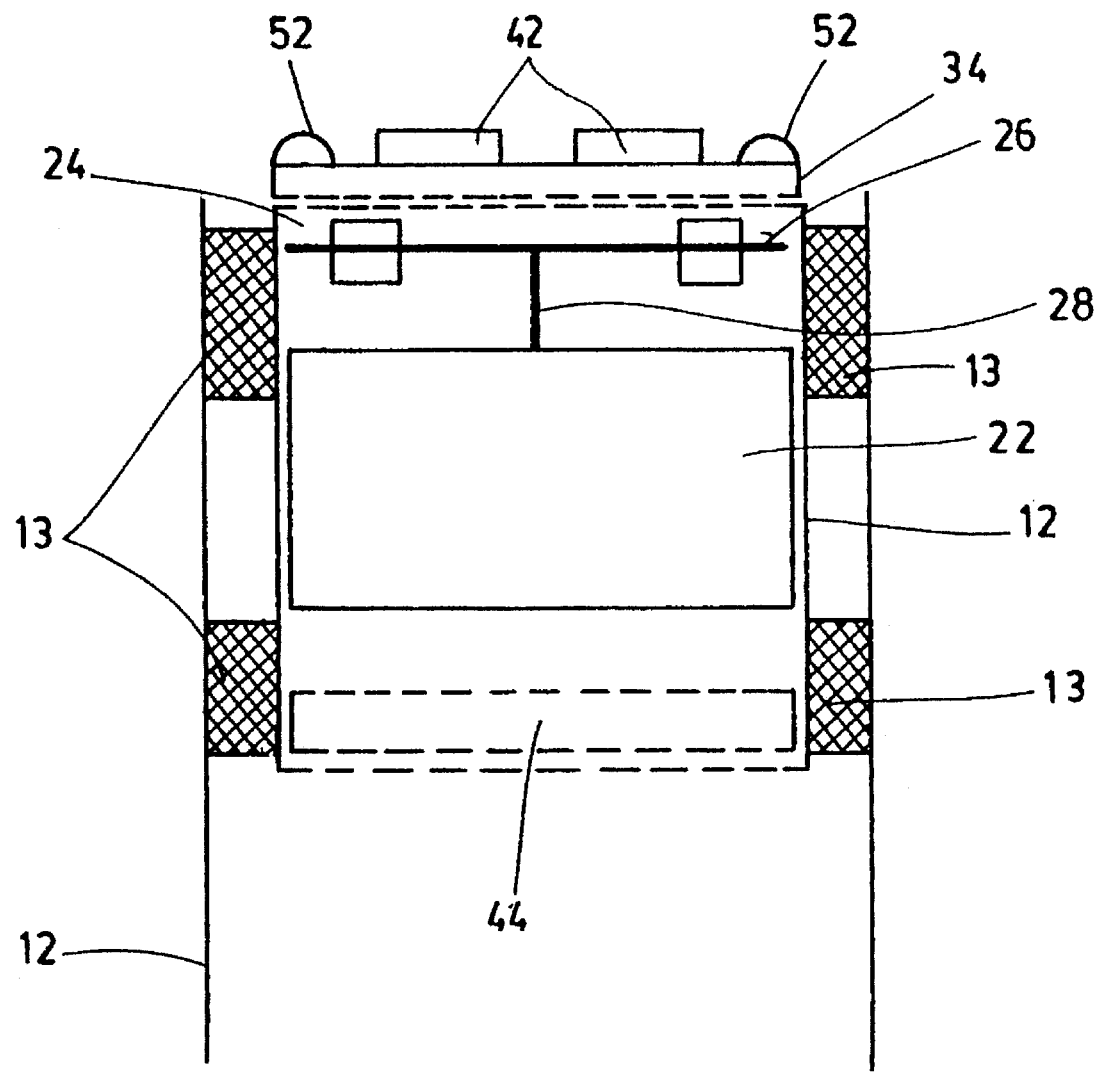
FIG. 3 is a cross-sectional view, similar to FIG. 1, of a further embodiment of the present invention.
Figure 5:
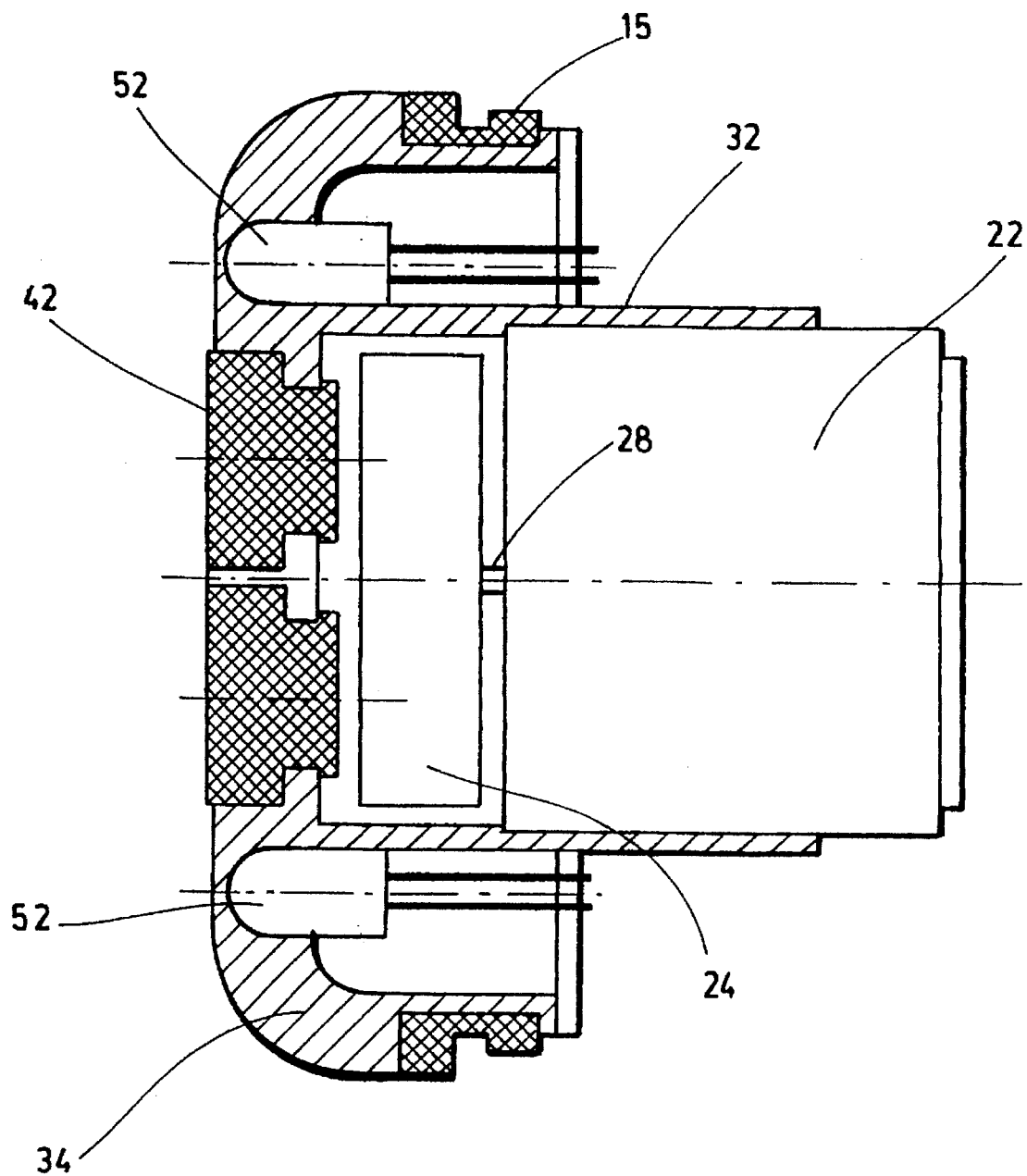
FIG. 5 is a cross-sectional view of the inner casing of another embodiment of the present invention.
Figure 6:
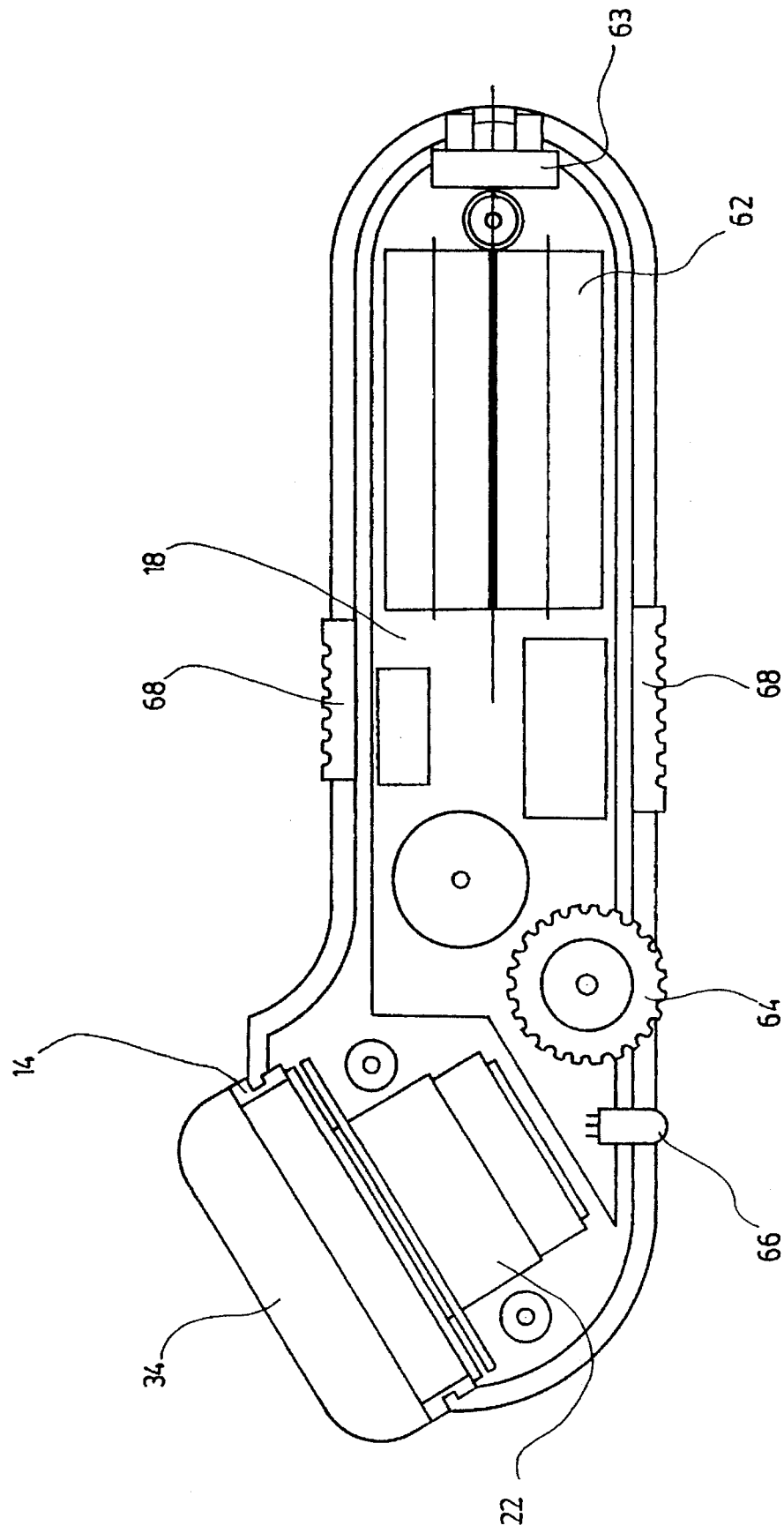
FIG. 6 is a side elevational view of another embodiment of the present invention, showing only the handle of the housing in cross section.

The device 10 for cosmetic and relaxation treatment according to the invention, as shown in the accompanying drawings, comprises a housing 12 preferably made of plastic material. The housing 12 has an aperture 14. Preferably, the housing 12 is portable and it defines a handle 18, as illustrated in FIG. 6, which allows easy manipulation of the device 10 with one hand. An electric motor 22 is located within the housing 12. The device 10 also comprises a plurality of magnets 24 facing the aperture 14 and mounted on a rotor 26. The rotor 26 is axially mounted on the shaft 28 connected to the motor 22. As illustrated in FIGS. 1 to 3, the rotor 26 and the shaft 28 are positioned within the housing 12 so that the rotor 26 faces the aperture 14 of the housing 12. In practice, the motor 22 can be directly fastened to the housing 12 by a resilient means such as elastic blocks 13. However, any other resilient means such as a rubber bushing 15, shown in FIGS. 5 and 6, may be used to fasten the motor 22 to the housing 12.

The device according to the present invention illustrated in FIGS. 1 to 3, preferably comprises an inner casing 32 in which the motor 22 is rigidly mounted. In this embodiment of the invention, it is the inner casing 32 which is resiliently fastened to the housing 12. In this embodiment, a device head 34 is connected to the inner casing 32 and is closing the aperture 14 of the housing 12. The rotor 26 is extending close to the device head 34.

In use, the head 34 is placed on the surface of the body that needs treatment. When the motor 22 is off and the rotor 26 is static, the magnets 24 generate a static magnetic field with no vibration. When the motor 22 is on upon rotation of the rotor 26, the magnets 24 start to revolve and then generate a dynamic magnetic field that has more pronounced effects compared with the static one. However, the static magnetic field is more gentle. Gentle vibrations are also produced when the motor 22 is on. As the inner casing 32 is resiliently fastened to the housing 12, most of the vibrations are transferred to the head 34 of the device 10 and not to the housing 12, nor to the handle 18 and, thus, allow a gentle massage of the skin surface in contact with the head 34. Consequently, the hand of the user is not unduly bothered by those vibrations.

Figure 4:
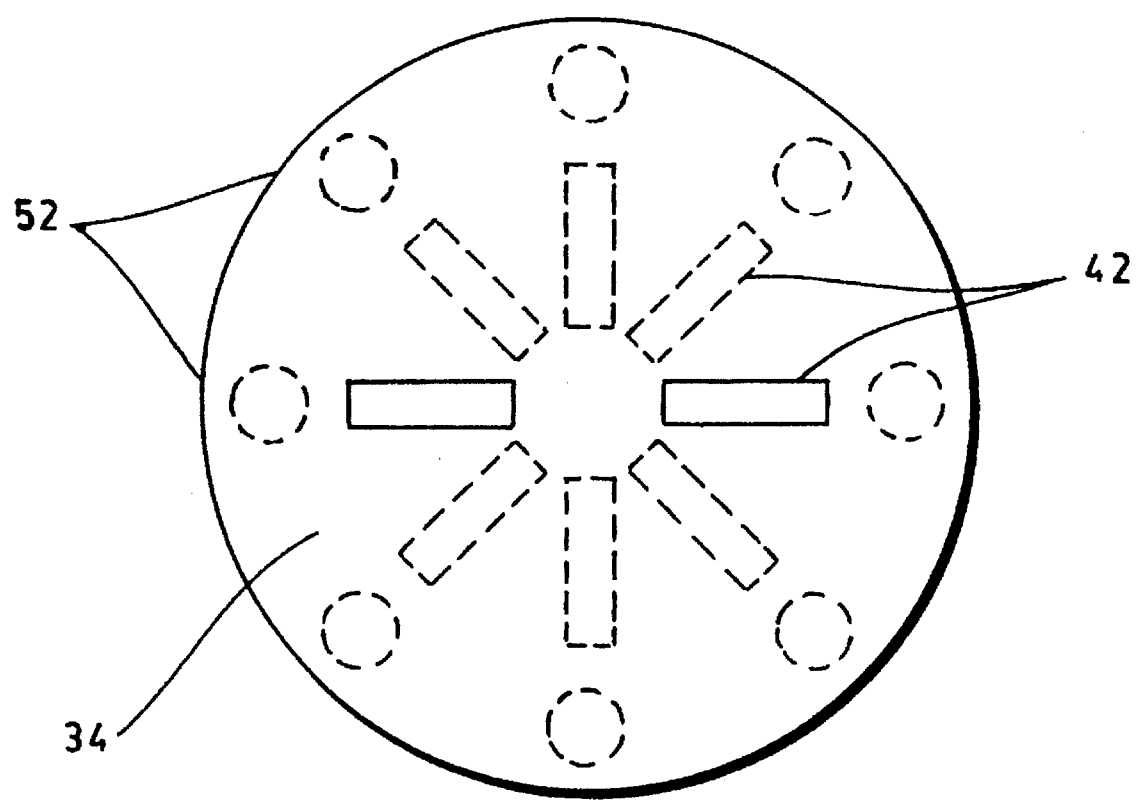
FIG. 4 is a top plan view of the head of the device shown in FIG. 3.

In order to increase the effect of the physical factors, the device 10 illustrated in FIG. 1 may be provided with at least two spaced-apart surface electrodes 42 mounted on the head 34 and connected to a generator 44, which produces electrical impulses and is mounted within the housing 12, as illustrated in FIG. 2. These electrodes 42 provide electrostimulation treatment by stimulating the skin and subcutaneous muscles. The device 10 may also be provided, as illustrated in FIG. 3, with a plurality of light emitting diodes 52 mounted on the head 34 and connected to the generator 44. If necessary, a second generator 44 may be used for the diodes 52. These diodes 52 ensure photostimulation of the exposed skin. As illustrated in FIG. 4, the diodes 52 and the electrodes 42 may be circumferentially distributed and spaced apart from each other.

In a preferred embodiment illustrated in FIG. 6 and wherein the motor is electric, the cosmetic device 10 further comprises means for providing electric power, such as a battery 62 located within the housing 12 and electrically connected to the motor 22 and to the generator 44. The battery 62 may be a regular battery or, preferably, a rechargeable battery. For recharging the rechargeable battery, the device 10 may further comprise a connector 63 within the housing 12 for connecting the battery 62 to an electrical charger (not illustrated).

For controlling the intensity of the electrostimulation, the device 10 may further comprise, on the handle 18, a manually operable potentiometer 64 connected to the electrodes 42 and to an ON/OFF indicating light 66. In use, the ON/OFF indicating light 66 turns red for warning the user that the generator 44 is on. The light 66 and control for the potentiometer 64 are located on the surface of the handle 18, allowing the user to easily see the light 66 and to control the voltage by simply rotating the potentiometer 64.

The generator 44 and the motor 22 may advantageously be connected with manually operable switches 68 located on the handle portion 18. A first switch is connected to the motor 22 and the second one is connected to the generator 44.

Although preferred embodiments of the invention have been described in detail herein and illustrated in the accompanying drawings, it is to be understood that the invention is not limited to these embodiments and that various changes and modifications may be effected therein without departing from the scope or spirit of the invention.

What is claimed is:

1. A device for cosmetic and relaxation treatment comprising:

a housing provided with an aperture;

a motor located within the housing;

an inner casing located inside the housing and in which is rigidly mounted the motor;

resilient means for resiliently locking said inner casing within said housing;

a shaft driven by the motor;

a rotor axially mounted onto the shaft, said shaft and rotor being positioned so that the rotor faces the aperture;

a plurality of magnets mounted onto the rotor; and a device head connected to the inner casing and closing the aperture of the housing, said device head extending close to the rotor; whereby said magnets generate a rotating magnetic field when the motor is on and a static magnetic field when the motor is off.

2. A device as claimed in claim 1, further comprising:

at least two spaced-apart surface electrodes mounted onto the device head; and a generator of electrical impulses located within the housing and connected to the electrodes.

3. A device as claimed in claim 2, further comprising:

a plurality of light emitting diodes mounted onto the device head, each of said diodes being connected to said generator.

4. A device as claimed in claim 3, wherein the diodes and the electrodes are circumferentially distributed and equally spaced apart from each other onto the device head.

5. A device as claimed in claim 4, wherein the housing is shaped to define a portable handle.

6. A device as claimed in claim 4, wherein said motor is electric and said device further comprises means for providing electrical power, said means being electrically connected to the motor and the generator.

7. A device as claimed in claim 6, wherein the means for providing electrical power comprises a battery located within the housing, the device further comprising means for electrically connecting the battery to an electrical charger.

8. A device as claimed in claim 7, further comprising:

a manually operable potentiometer connected to the electrodes; and an ON/OFF indicator light, said potentiometer and light being located on the handle.

9. A device as claimed in claim 8, further comprising:

a first manually operable switch connected to the generator; and a second manually operable switch connected to the motor, said switches being located on the handle of the device.

10. A device as claimed in claim 9, wherein the housing is made of plastic.

* * * * *